United States Patent [19]

Kanzaki et al.

[11] Patent Number: 5,251,475
[45] Date of Patent: Oct. 12, 1993

[54] METHOD AND APPARATUS FOR DETERMINING CONTENTS OF SALT AND WATER IN WATER-IN-OIL TYPE EMULSIFIED PRODUCT

[75] Inventors: Mikio Kanzaki; Toyohiko Doi; Hiroshi Nakanuma, all of Tokyo; Miyuki Shibuya, Saitama, all of Japan

[73] Assignee: Morinaga Milk Industry Co., Ltd., Tokyo, Japan

[21] Appl. No.: 769,286

[22] Filed: Oct. 1, 1991

[30] Foreign Application Priority Data

Oct. 2, 1990 [JP] Japan .................. 2-263063

[51] Int. Cl.$^5$ ............................ G01N 33/06
[52] U.S. Cl. ................................ 73/61.41
[58] Field of Search ............... 73/61.41, 53.02

[56] References Cited

U.S. PATENT DOCUMENTS 4,266,425  5/1981  Allport .................. 73/61.41
4,359,638 11/1982  Allport .................. 73/61.41
4,864,850  9/1989  Price ..................... 73/73

FOREIGN PATENT DOCUMENTS 0038254 10/1981 European Pat. Off. .

Primary Examiner—Hezron E. Williams
Assistant Examiner—Joseph W. Roskos
Attorney, Agent, or Firm—Armstrong, Westerman, Hattori, McLeland & Naughton

[57] ABSTRACT

A method and apparatus for determining the contents of salt and water in a water-in-oil type emulsified product are disclosed herein. In the method, two kinds of physical quantities which are related to the contents of water and salt in the water-in-oil type emulsified product and are capable of being measured in a short time are measured. Then, values of the contents of water and salt are calculated from the two physical quantities measured, by use of a bivariable multiple regression equation wherein the two physical quantities are used as explanatory variables and the contents of salt and water are used as objective variables.

3 Claims, 1 Drawing Sheet

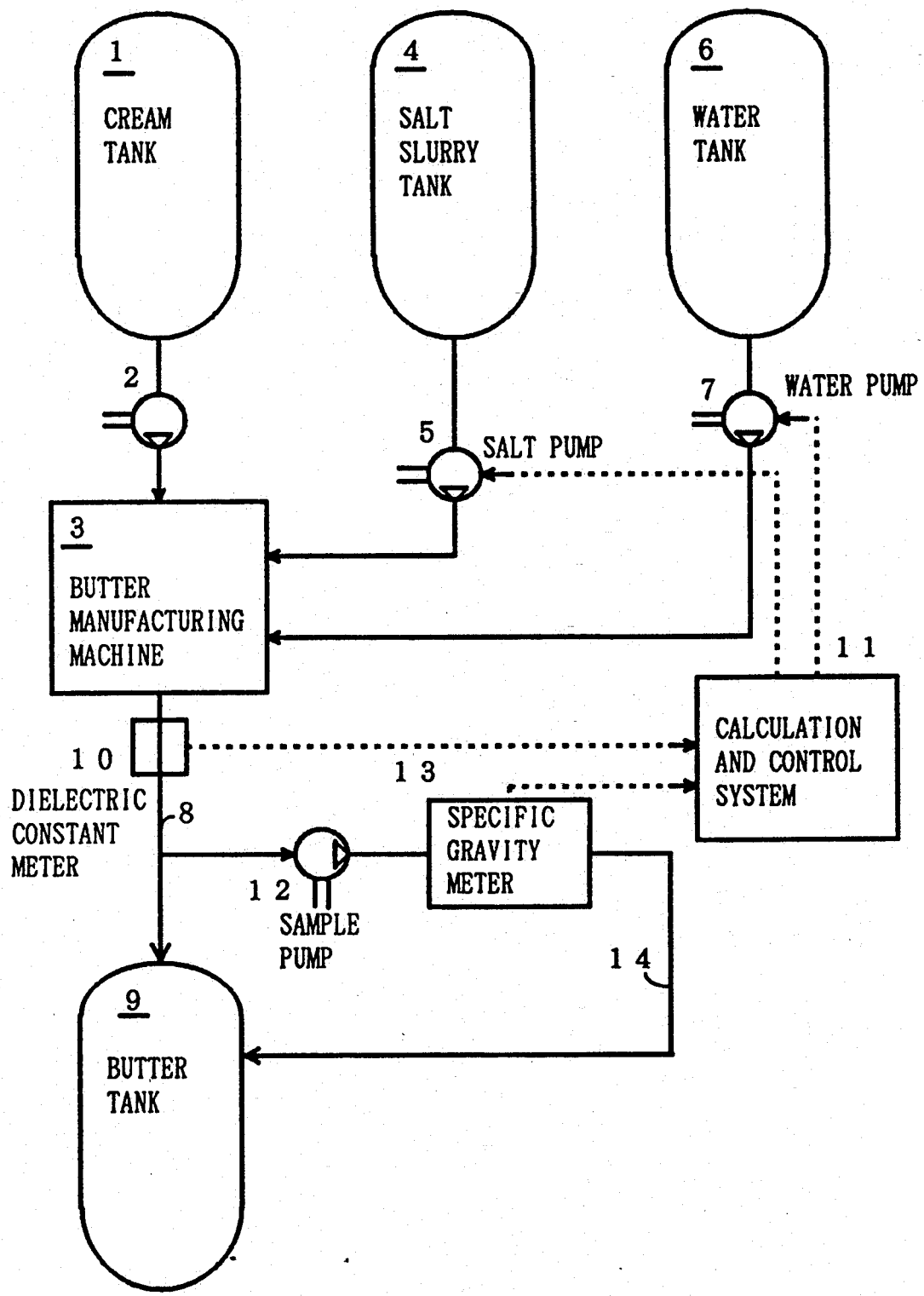

METHOD AND APPARATUS FOR DETERMINING CONTENTS OF SALT AND WATER IN WATER-IN-OIL TYPE EMULSIFIED PRODUCT

BACKGROUND OF THE INVENTION

1. Field of the Invention

The present invention relates to a method and apparatus for determining the contents of salt and water in a water-in-oil type emulsified product (which is a preparation comprised of an aqueous solution dispersed in a fat or oil). The water-in-oil type emulsified product includes a butter, a margarine and other spreads.

2. Description of the Prior Art

Salt and water contained in the water-in-oil type emulsified product are important components which decide the quality of the water-in-oil type emulsified product, and the examination of the dispersed state of the salt is also an item which is important for a quality control. Therefore, in order to control the contents of salt and water or the dispersed state of the salt, the determination of the contents of salt and water is frequently carried out in a manufacturing process.

The methods for determining the content of salt which have been conventionally used are (1) a method (Mohr's method) which comprises extracting a sample with water and titrating the extracted solution with a normal solution of silver nitrate, (2) a determining method which comprises extracting salt from a sample with water and measuring the content of salt in the extract by mean of a sodium ion meter or a chlorine ion meter, and (3) a method for measuring the content of salt by mean of $\gamma$ ray absorption technique. The methods for determining the content of water which have been conventionally used include (4) a drying method in content, (5) Karl Fischer method, (6) a method using a dielectric constant, and (7) a microwave absorption method.

However, the above prior art methods for determining the contents of salt or water contain several problems. Those are, as the methods for determining the salt content, the method (1) has complicated processes such as the extraction and the titration, and is time consuming, so it is not suitable for on-line analysis, the method (2) has the problem of a need for an extracting process, the problem of the accuracy of the ion meters and the problem of the contamination of the electrode with oil and the method (3) has the problems of safety handling, and food protection radiation. As the methods for determining the water content, the method (4) is an official and basic method specified in "Ministerial Ordinance relative to Specification or the like of Components of Milk and Milky Product", Japanese Welfare Ministry Ordinance No. 52, Dec. 27, 1951, but has problems that the measurement is of a batch type and time consuming and it is not suitable for on-line analysis. The method (5) is complicated in operation and high in analysis cost. In the method (6), when salts are dissolved in a water phase of an emulsified product, the salts content influences the dielectric constant, a water content cannot be obtained from dielectric constant alone. Thus, the water content cannot be determined with dielectric constant as a result of disturbance of salts.

In this way, the prior art methods are unsuitable for rapid and accurate determination of salt and water content.

Accordingly, the present inventors have made a search for rapid measureable physical quantities (measureable items from which salt and water content can be calculated. However, the suitable items cannot be found among known physical properties. Accordingly, the present inventors had made studies for methods for determining salt and water content by use of a plurality of measureable items which are not correlated to one another, and consequently have found that the intended purpose can be achieved by using a dielectric constant (or a relative dielectric constant or a microwave absorption index) and a specific gravity together.

More specifically, the present invention could be accomplished by finding the following respects (a) and (b):

(a) If the specific gravities and relative dielectric constants of components (i.e., salt and water) of a water-in-oil type emulsified product have specific value, are constant, the specific gravity and relative dielectric constant of the entire water-in-oil type emulsified product (i.e., two physical quantities of the water-in-oil type emulsified product) can be determined according to proportions of the individual components.

(b) Salt and water content the water-in-oil type emulsified product can be determined as criterion variables, if two physical quantities (e.g., a specific gravity and a relative dielectric constant) are used as explanatory variables.

The above (a) and (b) will be described using a margarine, as an example, which is a water-in-oil type emulsified product.

As described in "Solution Chemistry", pp. 116, Hitoshi Otaki (issued from Shoukabou, Sep. 30, 1985), a decrement in specific dielectric constant is represented by the following expression formula (1):

$$C(\delta_+ + \delta_-) \tag{1}$$

wherein C represents a content of an electrolyte, and $\delta_+ + \delta_-$ represent effects by a cation and an anion, respectively.

The components of a margarine which is a water-in-oil type emulsified product and the characteristic values of the components will be defined as given in Table 1.

TABLE 1

| Component | Composition (%) | S.G. | R.D.C. |
|---|---|---|---|
| Fatty oil | 100-M-N | $G_1$ | $C_1$ |
| Water | M | $G_2$ | $C_2$ |
| Salt | N | — | — |

S.G. = Specific gravity
R.D.C. = Relative dielectric constant

With a definition as given in Table 1, the specific gravity of the entire solution of salt contained in the margarine is represented approximately within a given range of variations by the following expression formula (2):

$$G_2 + [k \cdot N/(M+N)] \tag{2}$$

wherein k is an experience value and is a constant within such given range of variations.

Therefore, if the specific gravity of the entire margarine is represented by B, the value of B can be represented by the following expression formula (3):

$$B = G_1 \times (100 - M - N)/100 + [G_2 + kN/(M+N)] \times (M+N)/100 \tag{3}$$

On the other hand, the relative dielectric constant of the entire solution of salt contained in the margarine is represented by the following expression formula (4) in the same manner as with the expression formula (1):

$$C_2 - (\delta_+ + \delta_-)N/(M+N) \tag{4}$$

wherein $\delta_+$ and $\delta_-$ are reduction effect coefficients of relative dielectric constants of $Na^+$ and $Cl^-$ and are values found experimetally, respectively.

Because the solution of salt and the fatty oil are in a simple mixed state and the actually measurable range is narrow, an addability can be established. Therefore, the relative dielectric constant of the entire margarine is represented by the following expression formula (5):

$$A = C_1 \times (100 - M - N)/100 + [C_2 - (\delta_+ + \delta_-)N] \times (-N + M)/100 \tag{5}$$

By solving the above expressions (4) and (5) for M and N, the following expressions formulas (6) and (7) are provided:

$$N = 100[B(C_2 - C_1) - A(G_2 - G_1) + C_1(G_2 - G_1) - G_1(C_2 - C_1)]/[k(C_2 - C_1) + (\delta_+ + \delta_-) \times (G_2 - G_1)] \tag{6}$$

$$M = 100[B(C_2 - C_1 - \delta_+ - \delta_-) - A(G_2 - G_1 + k) + C_1(G_2 - G_1 + k) - G_1(C_2 - C_1 - \delta_+ - \delta_-)]/ - [(G_2 - G_1)(\delta_+ + \delta_-) - k(C_2 - C_1)] \tag{7}$$

The above expressions (6) and (7) indicate that the contents N and M of salt N and water M in the margarine (i.e., the water-in-oil type emulsified product) can be determined as objective variables (dependent variables), when the specific gravity and the relative dielectric constant of the water-in-oil type emulsified product are used as explanatory variables (independent variables).

It can be seen from the above description that if a bivariable multiple regression equation is employed, wherein the specific gravity and relative dielectric constant of the water-in-oil type emulsified product are used as explanatory variables, and the contents of salt and water in the water-in-oil type emulsified product are used as objective variables, the objective variables (the contents of salt and water) can be found. It can be also seen that the contents of salt and water can be found by employing the dielectric constant and specific gravity, or the microwave absorption index and specific gravity as two explanatory variables (i.e., two measureable physical quantities) according to a theory substantially similar to that described above.

SUMMARY OF THE INVENTION

Accordingly, it is an object of the present invention to provide a method and apparatus for determining the contents of salt and water in a water-in-oil type emulsified product, in which the contents of salt and water in the water-in-oil type emulsified product can be determined promptly and correctly and which can be incorporated into a process line and utilized for a line control.

To achieve the above object, according to the present invention, there is provided a method for determining the contents of salt and water in a water-in-oil type emulsified product, comprising the steps of measuring two physical quantities capable of being measured in a short time and concerning the contents of water and salt in the water-in-oil type emulsified product, and calculating values of the contents of water and salt from the two physical quantities measured, by use of a bivariable multiple regression equation wherein the two physical quantities are used as explanatory variables (independent variables) and the contents of salt and water are used as objective variables (dependent variables).

In the method for determining the contents of salt and water in a water-in-oil type emulsified product according the present invention, any one of the variables of a relative dielectric constant, a dielectric constant and a microwave absorption index of the water-in-oil type emulsified product and a specific gravity can be employed in combination as the two physical quantities capable of being measured in a short time.

The measurement of the two physical quantities has the following features (a) to (f), as compared with the direct measurement of the contents of salt and water:

(a) The measuring process is simple, and the time required for the measurement can be shortened substantially.

(b) The measurement can be easily automated.

(c) Continuous measurement is possible.

(d) The labor of analysis can be reduced.

(e) The method of the present invention can be utilized for an automatic control of components.

(f) The method of the present invention is a non-destructive inspection and hence, there is no loss in sample.

In addition, according to the present invention, there is provided an apparatus for determining the contents of salt and water in a water-in-oil type emulsified product, comprising a physical quantity detector means for measuring two physical quantities capable of being measured in a short time concerning the contents of the water and salt in the water-in-oil type emulsified product, and a calculating means for calculating values of the contents of the salt and water from the physical quantities measured, by use of a bivariable multiple regression equation wherein the two physical quantities are used as explanatory variables and the contents of salt and water are used as objective variables.

"The bivariable multiple regression equation wherein the two physical quantities are used as explanatory variables and the contents of salt and water are used as objective variables" can be previously obtained by a procedure comprising the following steps (A) and (B):

(A) A bivariable multiple regression equation (an equation having unknown regression coefficients) is established wherein two physical quantities of a first physical quantity selected from among a relative dielectric constant, a dielectric constant and a microwave absorption index; and a second physical quantity such as a specific gravity are used as explanatory variables, the contents of salt and water are used as objective variables.

(B) The two physical quantities are measured for a plurality of standard samples of water-in-oil type emulsified products having known contents of salt and water and similar to an analysis sample of a water-in-oil type emulsified product which is to be measured for the contents of salt and water therein. The regression coefficient is determined from data of the-thus-obtained measurements of the two physical quantities of the samples and values of the known contents of salt and water.

If the bivariable multiple regression equation found by the steps (A) and (B) is used, values of the contents of salt and water can be found by measuring the first and second physical quantities of the water-in-oil type emulsified product, substituting the results into the bivariable multiple regression equation and calculating.

The present invention will now be described in detail with a butter as an example of a water-in-oil type emulsified product.

The butter is produced by kneading a salt suspension into a butter mass (a salt-free butter material) resulting from agitation of a cream. Therefore, the specific gravity of the butter can be calculated in a weighted average of the specific gravity of the water, and the salt suspension and the butter-oil. The specific gravities of the components are as follows: 0.9 for the butter oil; 1.0 for water and 1.5 for a 50% salt suspension. Thus, the variation in specific gravity due to a variation in content of water is smaller, but the variation in specific gravity due to a variation in content of salt is larger. A usual butter has a salt content of 1 to 2% (all percentages cited herein are by weight) and a water content of about 15%. Therefore, a variation in salt content by 0.05% may be a variation in specific gravity by about 0.0005 which is sufficiently measureable.

On the other hand, the dielectric constants will now be considered. The dielectric constants of the components are as follows: 3 for the butter oil; 80 to 81 for water; 5.6 for salt (crystal). The dielectric constant value of water is remarkably large. Therefore, a slight variation in content of water largely influences on the dielectric constant. The salt itself is little different in dielectric constant from the butter oil and hence, the influence thereof is less, but it is known that if the salt is dissolved in water, the dielectric constant of the water is reduced. As described above, if the content of an electrolyte is represented by C, and effects by cation and anion are represented by $\delta_+$ and $\delta_-$, respectively, a decrement in relative dielectric constant can be represented by the above-described expression formula (1).

An influence due to a dispersed state will now be considered. As described in "Chemistry of Dispersed Emulsion System", by Fumio Kitahara and Kunio Furusawa (issued from Kougaku Tosho, Apr. 1, 1988), the dielectric nature of a dispersion system is influenced by the degree of dispersion flucculation and by the phase of W/O (water in oil) or O/W (oil in water), but less influenced by the particle size and particle size distribution of the dispersion system. In a stabilized butter, a dispersoid is a waterdroplet and therefore, no flucculation occurs, and no phase turnover of a continuous phase and a dispersion phase also occur. For these reasons, a variation in degree of dispersion flocculation and in W/O or O/W is scarcely observed and hence, it can be conceived that the measured relative dielectric constant is influenced only by components.

As apparent from the above description, a combination of the specific gravity and the relative dielectric constant is easily determined in correspondence with a combination of the contents of salt or water in the butter. For example, if the water content is constant and the salt content is increased, the specific gravity is largely increased, and the relatively dielectric constant is little varied or slightly reduced. In an inverse case, there are all inverse phenomena.

On the other hand, if the salt content is constant and the water content is increased, the specific gravity is slightly increased, but the relative dielectric constant is largely increased. In an inverse case, there are all inverse phenomena.

Therefore, to determine the contents of salt and water from the determined relative dielectric constant and specific gravity, a simultaneous equation having two unknown qualities may be solved. Methods for actually solving the above simultaneous equation include a method for solving a multiple regression equation by a method of least squares from measurements of a relative dielectric constant (or a dielectric constant or a microwave absorption index) and a specific gravity of a sample whose contents of salt and water are already known.

When the multiple regression equation is solved by the method of least squares, a procedure according to the present invention may be carried out. More specifically, first, the contents of salt and water are measured for plural standard samples of the same type as an analysis sample a conventional method, and then the dielectric constant and specific gravity are measured with a method actually used. Thus-obtained measurements are subjected to a method of least squares, thereby establishing a multiply regression equation capable of calculating values of the contents of salt and water from the values of dielectric constant and the specific gravity.

Then, the determination of the contents of salt and water in the analysis sample (water-in-oil emulsified product) is achieved by measuring the relative dielectric constant and the specific gravity of the analysis sample and substituting the resulting measurements into the multiple regression equation to calculate values of the contents of salt and water. One example of such calculation will be described in "Description of the Preferred Embodiment" which will be described hereinafter.

The above and other objects, features and advantages will become clear from a reading of the following description of the preferred embodiment, taken in conjunction with the accompanying drawing.

BRIEF DESCRIPTION OF THE DRAWING

FIG. 1 depicts an apparatus according to the present invention measuring dielectric constant and specific gravity applied to a line control for a butter manufacturing process.

FIG. 2 depicts an apparatus according to the present invention measuring microwave absorption index and specific gravity applied to a line control for a butter manufacturing process.

DESCRIPTION OF THE PREFERRED EMBODIMENT

The present invention will now be described by way of a preferred embodiment in connection with the accompanying drawing.

In this embodiment, a dielectric constant and a specific gravity are employed as the above-described two explanatory variables (i.e., two measurable physical quantities).

FIG. 1 illustrates a water-in-oil type emulsified product manufacturing apparatus (i.e., a butter manufacturing apparatus) which is designed to control the contents of salt and water by application of the present invention to a process for producing a butter as a water-in-oil type emulsified product.

Cream in a cream tank 1 can be pumped into a butter manufacturing machine 3 by a cream pump 2. A salt slurry in a salt slurry tank 4 can be pumped into the butter manufacturing machine 3 by a salt pump 5. Water in a water tank 6 is pumped into the butter manufacturing machine 3 by a water pump 7.

Butter discharged from the butter manufacturing machine 3 is transferred through a butter transfer pipe 8 into a butter tank 9. A dielectric constant meter electrode 10 is disposed in the butter transfer pipe 8, so that the dielectric constant of the butter passed therethrough is measured, and the measured dielectric constant is supplied to a calculation and control system 11. The butter transfer pipe 8 is provided with a branch pipeline 14 which is connected via a sample pump 12 and a specific gravity meter 13 to the butter tank 9. A signal indicative of the specific gravity detected by the specific gravity meter 13 is applied to the calculation and control system 11. This calculation and control system 11 calculates values of the contents of salt and water from the input dielectric constant and specific gravity, and a method of such calculation (a calculating equation) will be described hereinafter. The calculation and control system 11 delivers signals indicative of commands to control the operation of the salt pump 5 and the water pump 7 in accordance with the calculated content values. Then, the salt pump 5 and the water pump 7 are operated by the output control signals, so that the amounts of salt slurry and water supplied to the butter machine 3 are controlled. Each of dotted lines in FIG. 1 indicates a signal path. The dielectric constant meter 10 and specific gravity meter 13 used may be those commercially available. Alternatively, a microwave absorption index measuring instrument may be used in place of the dielectric constant meter 10.

Description will now be made of a method for controlling the contents of salt and water by use of the water-in-oil type emulsified product manufacturing apparatus, i.e., the butter manufacturing apparatus shown in FIG. 1.

The contents of salt and water, dielectric constant and specific gravity of 11 butter samples (which are standard samples) previously made with the butter manufacturing apparatus was measured. In this case, the analysis of the salt was carried out in a Mohr's method for water extraction of samples. The content of water was measured by means of the drying and weight-reducing method (the above-described official method specified in Japanese Welfare Ministry Ordinance). Further, the dielectric constant was measured using Ag4311 LCR METER made by Andou Denki Co. equipped with a measuring cell which is comprised of 5 mm thick acryl plate having seven holes of 6 mm diameter provided therein within a range of an equilateral triangle of a side length of 45 mm and which is clamped in a vertically sandwiched manner between 50 mm × 70 mm long and 4 mm wide insulating stainless plates. The specific gravity was measured at 30° C. by used of DA-300 made by Kyoto Denshi Co., as the specific gravity against to water of temperature 4° C. These measuring results are given in Table 2.

TABLE 2

| Standard sample No. | Salt (%) | Water (%) | Dielectric constant (pF) | Specific gravity |
|---|---|---|---|---|
| 1 | 1.51 | 15.85 | 4.28 | 0.9417 |
| 2 | 1.45 | 16.03 | 4.60 | 0.9413 |
| 3 | 1.44 | 16.08 | 4.72 | 0.9411 |
| 4 | 1.53 | 15.72 | 4.41 | 0.9418 |
| 5 | 1.53 | 15.79 | 4.40 | 0.9416 |
| 6 | 1.55 | 16.11 | 4.35 | 0.9423 |
| 7 | 1.38 | 16.76 | 4.80 | 0.9412 |

TABLE 2-continued

| Standard sample No. | Salt (%) | Water (%) | Dielectric constant (pF) | Specific gravity |
|---|---|---|---|---|
| 8 | 1.52 | 15.53 | 4.15 | 0.9415 |
| 9 | 1.48 | 15.86 | 4.37 | 0.9415 |
| 10 | 1.44 | 15.94 | 4.53 | 0.9412 |
| 11 | 1.43 | 16.04 | 4.50 | 0.9412 |

These results were subjected to a multiple regression analysis using a method of least squares, thereby providing a multiple regression equation for calculating values of contents of salt and water from values of dielectric constant and specific gravity. A precess to introduce the multiple regression equation is as follows:

On the assumption that a multiple regression equation for finding proportions N and M (%), salt and water content by weight respectively from the measuring results of the dielectric constant and specific gravity of the butter are represented by the expressions (8) and (9), coefficients in this equation are found in the following manner:

$$N = a_n + b_n C_i + d_n G_1 \tag{8}$$

$$M = a_m + b_m C_i + d_m G_1 \tag{9}$$

wherein $i = 1, 2, \cdots 11$.

The measuring results in Table 2 will be considered as being replaced by characters as given in Table 3.

TABLE 3

| Standard sample No. | Salt (%) | Water (%) | Dielectric constant (pF) | Specific gravity |
|---|---|---|---|---|
| 1 | N1 | M1 | C1 | G1 |
| 2 | N2 | M2 | C2 | G2 |
| 3 | N3 | M3 | C3 | G3 |
| 4 | . | . | . | . |
| 5 | . | . | . | . |
| 6 | . | . | . | . |
| 7 | Ni | Mi | Ci | Gi |
| 8 | . | . | . | . |
| 9 | . | . | . | . |
| 10 | . | . | . | . |
| 11 | N11 | M11 | C11 | G11 |

In Table 3, when averages of Ni, Mi, Ci and Gi are represented by Na, Ma, Ca and Ga, respectively, each variances thereof can be represented by the following expression formulas (10) to (13):

$$S_N^2 = (1/11) \sum_{i=1}^{i=11} (Ni - Na)^2 \tag{10}$$

$$S_M^2 = (1/11) \sum_{i=1}^{i=11} (Mi - Ma)^2 \tag{11}$$

$$S_C^2 = (1/11) \sum_{i=1}^{i=11} (Ci - Ca)^2 \tag{12}$$

$$S_G^2 = (1/11) \sum_{i=1}^{i=11} (Gi - Ga)^2 \tag{13}$$

And each covariances $S_{NG}$, $S_{NC}$, $S_{MG}$, $S_{MC}$ and $S_{CG}$ can be represented by the following expression formulas (14) to (18):

$$S_{NG} = (1/11) \sum_{i=1}^{i=11} (Ni - Na)(Gi - Ga) \tag{14}$$

-continued $$S_{NC} = (1/11) \sum_{i=1}^{i=11} (Ni - Na)(Ci - Ca) \quad (15)$$

$$S_{MG} = (1/11) \sum_{i=1}^{i=11} (Mi - Ma)(Gi - Ga) \quad (16)$$

$$S_{MC} = (1/11) \sum_{i=1}^{i=11} (Mi - Ma)(Ci - Ca) \quad (17)$$

$$S_{CG} = (1/11) \sum_{i=1}^{i=11} (Gi - Ga)(Ci - Ca) \quad (18)$$

Here, correlation coefficients are defined as given in Table 4 below.

TABLE 4

|  | Water | Specific gravity | Dielectric constant |
|---|---|---|---|
| Salt |  | $\gamma_{NG}$ | $\gamma_{NC}$ |
| Dielectric constant | $\gamma_{MC}$ | $\gamma_{CG}$ |  |
| Specific gravity | $\gamma_{MG}$ |  |  |

Then, the corelation coefficients $\gamma_{NG}$, $\gamma_{NC}$, $\gamma_{MG}$, $\gamma_{MC}$ and $\gamma_{CG}$ can be represented by the following expression formulas (19) to (23):

$$\gamma_{NG} = S_{NG}/(S_N \cdot S_G) \quad (19)$$

$$\gamma_{NC} = S_{NC}/(S_N \cdot S_C) \quad (20)$$

$$\gamma_{MG} = S_{MG}/(S_M \cdot S_G) \quad (21)$$

$$\gamma_{MC} = S_{MC}/(S_M \cdot S_C) \quad (22)$$

$$\gamma_{CG} = S_{CG}/(S_C \cdot S_G) \quad (23)$$

With these values, each coefficients in the multiple regression equations (8) and (9) can be represented by the following expression formulas:

$$b_n = (S_N/S_C) \times (\gamma_{NC} - \gamma_{NG} \times \gamma_{CG})/(1 - \gamma_{CG})^2 \quad (24)$$

$$d_n = (S_N/S_G) \times (\gamma_{NG} - \gamma_{NC} \times \gamma_{CG})/(1 - \gamma_{CG})^2 \quad (25)$$

$$a_n = Na - b_n \times Ca - d_n \times Ga \quad (26)$$

$$b_m = (S_M/S_C) \times (\gamma_{MC} - \gamma_{MG} \times \gamma_{CG})/(1 - \gamma_{CG})^2 \quad (27)$$

$$d_m = (S_M/S_G) \times (\gamma_{MG} - \gamma_{MC} \times \gamma_{CG})/(1 - \gamma_{CG})^2 \quad (28)$$

$$a_m = Ma - b_m \times Ca - d_m \times Ga \quad (29)$$

If the characters Ni, Mi, Ci and Gi in the expressions (10) to (18) are replaced by the values given in Table 2, and the characters Na, Ma, Ca and Ga are replaced by average values obtained from Table 2 and further, if the resulting values are substituted into the expressions (19) to (23), the following values are provided:

$S_N = 0.0513$
$S_M = 0.2985$
$S_C = 0.1819$
$S_G = 3.369 \times 10^{-4}$
$\gamma_{NC} = -0.8212$
$\gamma_{NG} = 0.8455$
$\gamma_{MC} = 0.8070$
$\gamma_{MG} = -0.2799$
$\gamma_{CG} = -0.6104$ These actual values are substituted into the expressions (24) to (29) to give the following coefficients.
$b_n = -0.1372$
$d_n = 83.54$
$a_n = -76.56$
$b_m = 1.664$
$d_m = 300.4$
$a_m = -274.3$ From these values and the above expression formulas (8) and (9), the following equations (30) and (31) are obtained.

$$N = -0.1372C + 83.54G - 76.56 \quad (30)$$

$$M = 1.664C + 300.4G - 274.3 \quad (31)$$

wherein N is a content of salt (%); M is a content of water (%); C is a dielectric constant (pF) and G is a specific gravity. The multiple regression coefficients of salt and water, each of which is an indication of the quality of a regression, were of 0.929 and 0.851, respectively.

Then, the dielectric constant and the specific gravity of each of 16 analysis samples were measured in the same manner as standard samples, and the resulting values were substituted into the regression equations (30) and (31) to calculate the contents of salt and water. The results are given in Table 5 with values resulting of drying method and Mohr's method.

TABLE 5

| Analysis sample No. | Salt (%) Conventional | Salt (%) Pres. Inve. | Water (%) Conventional | Water (%) Pres. Inve. |
|---|---|---|---|---|
| 21 | 1.53 | 1.53 | 16.24 | 16.16 |
| 22 | 1.56 | 1.57 | 16.06 | 16.09 |
| 23 | 1.48 | 1.49 | 15.92 | 15.87 |
| 24 | 1.60 | 1.57 | 16.15 | 16.10 |
| 25 | 1.61 | 1.61 | 15.95 | 16.01 |
| 26 | 1.53 | 1.54 | 15.87 | 15.89 |
| 27 | 1.66 | 1.65 | 16.03 | 15.98 |
| 28 | 1.59 | 1.57 | 16.07 | 16.12 |
| 29 | 1.57 | 1.59 | 15.91 | 15.88 |
| 30 | 1.63 | 1.63 | 15.87 | 15.79 |
| 31 | 1.63 | 1.61 | 16.95 | 16.91 |
| 32 | 1.60 | 1.61 | 16.10 | 16.16 |
| 33 | 1.55 | 1.55 | 15.96 | 15.92 |
| 34 | 1.57 | 1.58 | 15.81 | 15.76 |
| 35 | 1.49 | 1.48 | 15.98 | 15.89 |
| 36 | 1.52 | 1.52 | 15.82 | 15.76 |

Pres. Inve. = Present invention

It can be seen from the results in Table 5 that values of contents of salt and water can be obtained with a sufficient satisfactory accuracy by the method according to the present invention.

What is claimed is:

1. A method for controlling the contents of salt and water, respectively, in a water-in-oil emulsified composition produced in a continuous production line, comprising the steps of:
  a) measuring two physical parameter of specific gravity and dielectric constant or microwave absorption index, which correlates to the contents of salt and water in a plurality of water-in-oil emulsified compositions having known salt and water contents, whereby a set of measured parameters and known salt and water contents are determined;
  b) subjecting the set of measured parameters and known salt and water contents to a bivariable multiple regression analysis, thereby determining a first equation for calculating salt content and a second equation for calculating water content in a waterin-oil emulsified composition from the two physical parameters;

c) directly measuring the two physical parameters in the continuous water-in-oil emulsified composition production line;

d) determining the respective contents of salt and water in the water-in-oil emulsified composition production line having unknown salt and water content, by applying the two physical parameters measured in step (c) to the first and the second equations determined in step (b); and e) adjusting the amount of water and salt slurry, respectively, added to the continuous water-in-oil emulsified composition production line based on the salt and water contents determined in step (d).

2. An apparatus for controlling the contents of salt and water in a continuous production line for a water-in-oil emulsified composition, comprising a means for supplying water to the continuous production line;

a means for supplying a salt slurry to the continuous production line;

a means for measuring a first variable which correlates to the salt and water content of the water-in-oil emulsified composition, the means for measuring the first variable being positioned on the continuous production line and producing a first signal corresponding to the value of the first variable;

a means for measuring a second variable which correlates to the salt and water content of the water-in-oil emulsified composition, the means for measuring the second variable being positioned on the continuous production line and producing a second signal corresponding to the value of the second variable; and means for calculating the salt and water content in the water-in-oil emulsified composition by doing a bivariable multiple regression analysis on said first and second signals for water-in-oil emulsions having known salt and water content, to produce two equations from which the salt and water contents of the water-in-oil emulsified composition in the production line are calculated from the first and second signals, the means for calculating the salt and water content further producing a third signal for controlling the means for supplying water and a fourth signal for controlling the means for supplying the salt slurry, based on the salt and water content calculated.

3. An apparatus for controlling the contents of salt and water in a continuous production line for a water-in-oil emulsified composition according to claim 2, wherein specific gravity is employed as said first variable and dielectric constant or microwave absorption index is employed as said second variable.

* * * * *